United States Patent
Shrawat et al.

(10) Patent No.: US 8,829,210 B2
(45) Date of Patent: Sep. 9, 2014

(54) PROCESS FOR PREPARING DOCETAXEL AND ITS HYDRATE

(75) Inventors: Vimal Kumar Shrawat, Raichur (IN); Rafiuddin, Raichur (IN); Veereshappa, Raichur (IN); Prashant Purohit, Raichur (IN)

(73) Assignee: Shilpa Medicare Limited, Raichure, Karnataka (IN)

( * ) Notice: Subject to any disclaimer, the term of this patent is extended or adjusted under 35 U.S.C. 154(b) by 0 days.

(21) Appl. No.: 13/634,612

(22) PCT Filed: Aug. 29, 2011

(86) PCT No.: PCT/IN2011/000588
§ 371 (c)(1),
(2), (4) Date: Sep. 13, 2012

(87) PCT Pub. No.: WO2012/131698
PCT Pub. Date: Oct. 4, 2012

(65) Prior Publication Data
US 2014/0039209 A1 Feb. 6, 2014

(30) Foreign Application Priority Data
Apr. 1, 2011 (IN) .......................... 1117/CHE/2011

(51) Int. Cl.
*C07D 305/14* (2006.01)
*A61K 31/337* (2006.01)

(52) U.S. Cl.
CPC ............ *C07D 305/14* (2013.01); *A61K 31/337* (2013.01)
USPC .......................................... 549/510; 549/200

(58) Field of Classification Search
CPC ..................................................... C07D 305/14
USPC ................................................. 549/200, 510
See application file for complete search history.

(56) References Cited

U.S. PATENT DOCUMENTS

| | | | |
|---|---|---|---|
| 4,814,470 A | 3/1989 | Colin et al. | |
| 4,924,012 A | 5/1990 | Colin et al. | |
| 6,191,287 B1 | 2/2001 | Holton et al. | |
| 6,596,880 B1 * | 7/2003 | Fouque et al. | 549/510 |
| 6,900,342 B2 * | 5/2005 | Sharma et al. | 549/510 |
| 7,247,738 B2 * | 7/2007 | Sharma et al. | 549/510 |
| 7,662,980 B2 * | 2/2010 | Liao et al. | 549/510 |
| 8,686,165 B2 * | 4/2014 | Gurjar et al. | 549/510 |

FOREIGN PATENT DOCUMENTS

EP 0253738 1/1988

OTHER PUBLICATIONS

Kanazawa et al, Highly Stereocontrolled and Efficient Preparation of the Protected, Esterification-Ready Docetaxel (Taxotere) Side Chain, J. Org. Chem. 1994, 59, 1238-1240.

* cited by examiner

*Primary Examiner* — Golam M M Shameem

(57) ABSTRACT

The present invention provide process of preparation of (2R, 3S)—N-carboxy-3-phenylisoserine, N-tert-butyl ester, 13-ester with 5(β)-20-epoxy-1,2(α),4,7(β),10(β),13(α)-hexa hydroxy tax-11-en-9-one 4-acetate 2-benzoate or docetaxel and its trihydrate (I)

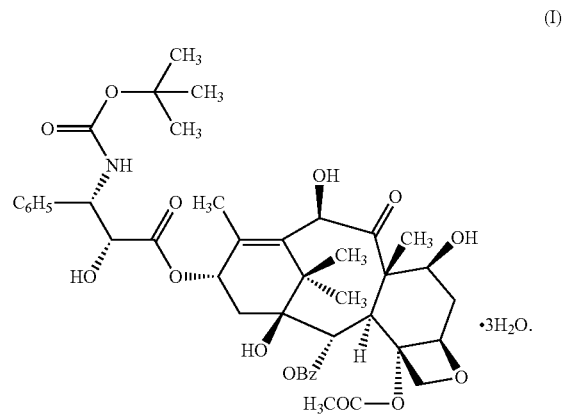

12 Claims, No Drawings

PROCESS FOR PREPARING DOCETAXEL AND ITS HYDRATE

FIELD OF THE INVENTION

Particular aspects of the present specification relate to the process for preparing of docetaxel and its hydrate.

BACKGROUND OF THE INVENTION

Docetaxel is an anti-neoplastic agent of taxoid family and is well-known to exhibit anti-tumor and antileukaemic properties. Presently, it is sold under the trade name TAXOTERE®.

DOCETAXEL is the generic name for the compound (2R, 3S)—N-carboxy-3-phenylisoserine, N-tert-butyl ester, 13-ester with 5(β)-20-epoxy-1,2(α),4,7(β),10(β),13(α)-hexahydroxy tax-11-en-9-one 4-acetate 2-benzoate, trihydrate and is represented by the formula (I)

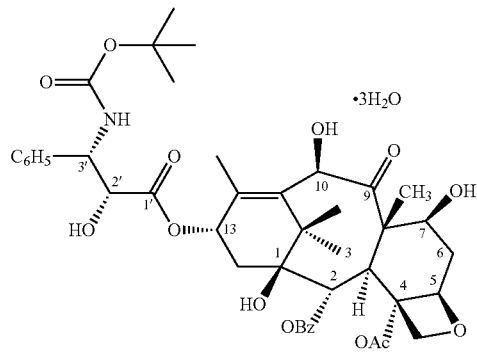

Quite often, the key starting material used for preparing docetaxel is 10-DAB (10-De-acetyl Baccatin), which is extracted from the needles of the yew plant (*Taxus baccata*). Since in 10-DAB, which is possessing many hydroxy groups and all hydroxy groups are not equally reactive under the same reaction conditions, it is quite unpredictable as to which particular condition may work and industrially viable for the desired selective derivatization during the conversion of 10-DAB to taxane/taxane derivatives like docetaxel or paclitaxel.

In particular for docetaxel, vast literature reveals that the preparation of docetaxel from 10-DAB requires quite often selective protection of the C (7) and the C(10) hydroxy groups before the attachment of the side chain at C(13) hydroxy function.

Senilh et al. in *C.R. Acad. Sci. Paris, IT,* 1981, 293,501 observed that the relative reactivity of the four hydroxy groups in the 10-DAB is C (7)-OH>C (10)-OH>C(13)-OH>C(1)-OH towards acetic anhydride in pyridine, indicating that C (7)-OH reactivity magnitude is among the highest.

Holten et al. in U.S. Pat. No. 6,191,287 disclosed that the relative reactivity of C (7) and C (10) in 10 DAB is different for acetic anhydride in the presence of a lewis acid than a base. C (10) hydroxy group may be protected prior to the C (7) hydroxy group. Holten et al. described a process for acylating or silylating the C (10) hydroxy group prior to acylating, silylating or ketalizing the C (7) hydroxy group.

In European patent application EP 253,738B1 and its corresponding equivalent U.S. Pat. No. 4,814,470, the product of general formula (I) and their preparation have been described as first synthesis involving the use of cinnamoyl chloride for side chain incorporation based on the following synthetic scheme—

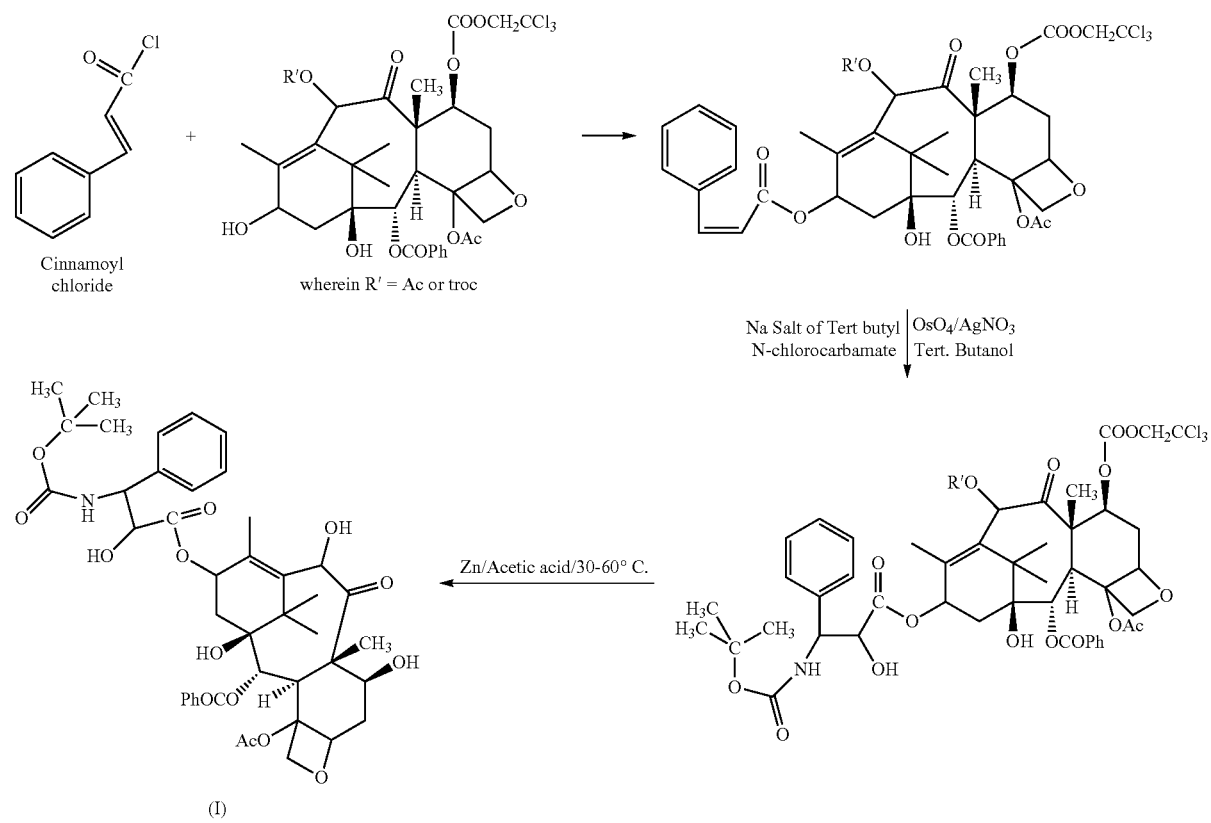

Colin et al in U.S. Pat. No. 4,924,012 disclose a process for preparing docetaxel, wherein an acid such as threo-2-(1-Ethoxyethoxy)-3-tert-butyloxycarbonylamino-3-phenylpropionic acid is condensed with a taxane derivative in which R2 is an acetyl group or a hydroxy-protecting group and R3 is a hydroxy-protecting group, and the protecting groups $R_1$, $R_3$ and where appropriate R2 is replaced by hydrogen.

The removal of the protecting groups from the ester obtained was accomplished by means of zinc in the presence of acetic acid at a temperature of between 30° and 60° C. or by treatment by means of an acid (inorganic or organic) such as hydrochloric acid or acetic acid dissolved in an aliphatic alcohol containing 1 to 3 carbon atoms in the presence of zinc. The reaction may be summarized based on the following synthetic scheme—

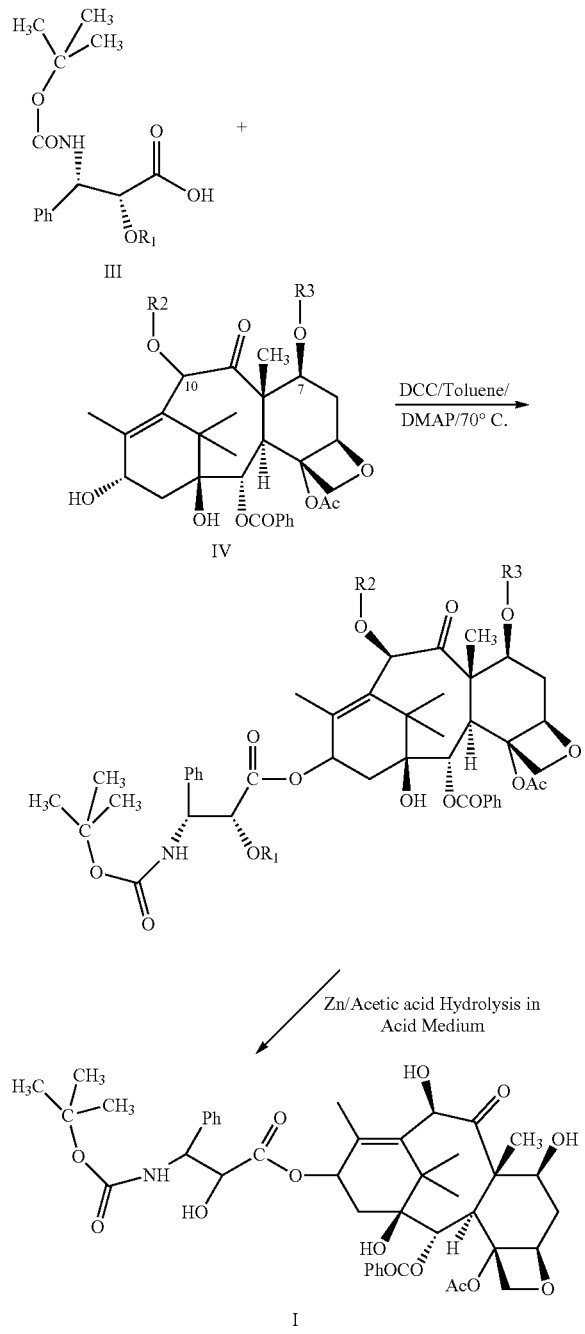

Fouque et al in U.S. Pat. No. 6,596,880 disclosed the method for the preparation of taxane derivatives including docetaxel comprising esterification at a temperature between −10 and 60° C. of a derivative of baccatin-III or 10-deacetyl baccatin-III of general formula (II) by means of an acid of general formula (III), followed by replacement of the protective groupings of the resulting product by hydrogen atoms.

The reaction may be summarized based on the following synthetic scheme—

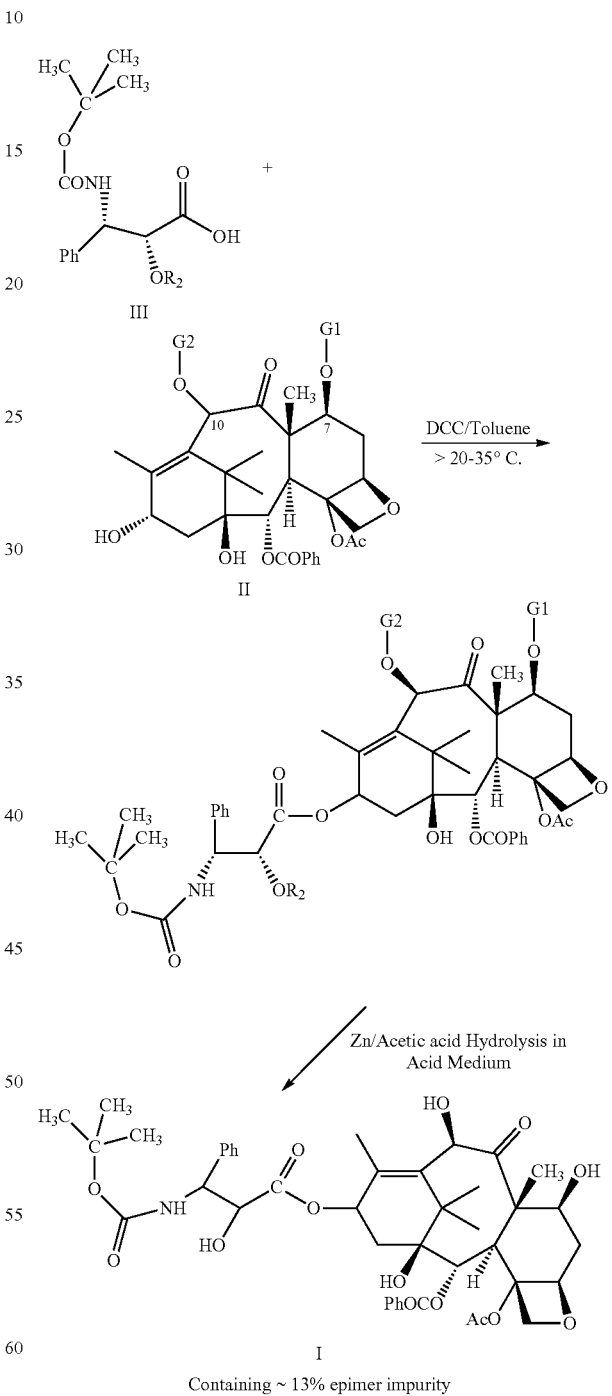

Containing ~ 13% epimer impurity

The specification particularly describes the following specific aspects of the process of invention the as—
i. Esterification of the alcohol of general formula (II) using the acid of general formula (III)

may be performed at a temperature preferably between 20 and 35° C.

ii. For esterification, Esters and aromatic hydrocarbons are very particularly advantageous.

iii. In general formula (II) and (III), the protecting groups G1, G2 and R2 are selected from
  a. G1—2,2,2-trichloroethoxycarbonyl radical or a trialkylsilyl radical in which each
     alkyl part contains 1 to 4 carbon atoms,
  b. G2—2,2,2-trichloroethoxycarbonyl radical
  c. R2— methoxymethyl, 1-ethoxyethyl, benzyloxymethyl, (β-trimethyl silyl ethoxy)methyl,
     tetrahydropyranyl, 2,2,2-trichloroethoxymethyl or 2,2,2-trichloro
     ethoxy carbonyl radical iv. Replacement of the protecting groups by hydrogen atoms is carried out using zinc in acetic
    acid or by hydrolysis in an acidic medium.

Kanazawa et al in *J. Org. Chem.* 1994, 59, 1238-1240 disclosed another process for preparing docetaxel from the side chain free acid (A) with reasonably high efficiency based on the following synthetic scheme—

Its esterification with 7,10-bis[(2,2,2-trichloroethoxy)carbonyl]-10-desacetylbaccatin III was carried out in toluene with DCC and DMAP to provide after purification the triply protected docetaxel derivative. This triply protected docetaxel derivative is deprotected into Docetaxel through first treatment with zinc copper couple in acetic acid-methanol and then with hydrogen in the presence of palladium black.

However, in this process, docetaxel so produced was found to be contaminated with up to 15% of the corresponding 2'S (epimer) derivative. The formation of this epimer, which occurs during esterification, is apparently unavoidable and their removal required a tedious and industrially non viable chromatographic means. Though there have been many advances in the field especially utilizing direct coupling with open chain isoserine derivatives as well as indirect ways involving blocked side chains like oxazolidone, β-lactam, Oxazoline, Oxazinone and the like and later on opening the blocked side chain ring structures, however, there still remains a need for new or improved, economically viable processes for the preparation of docetaxel, which may be simple and amenable to scale up. The present invention addresses these needs and provides further related advantages like less epimer impurities formation and simple workup in the steps.

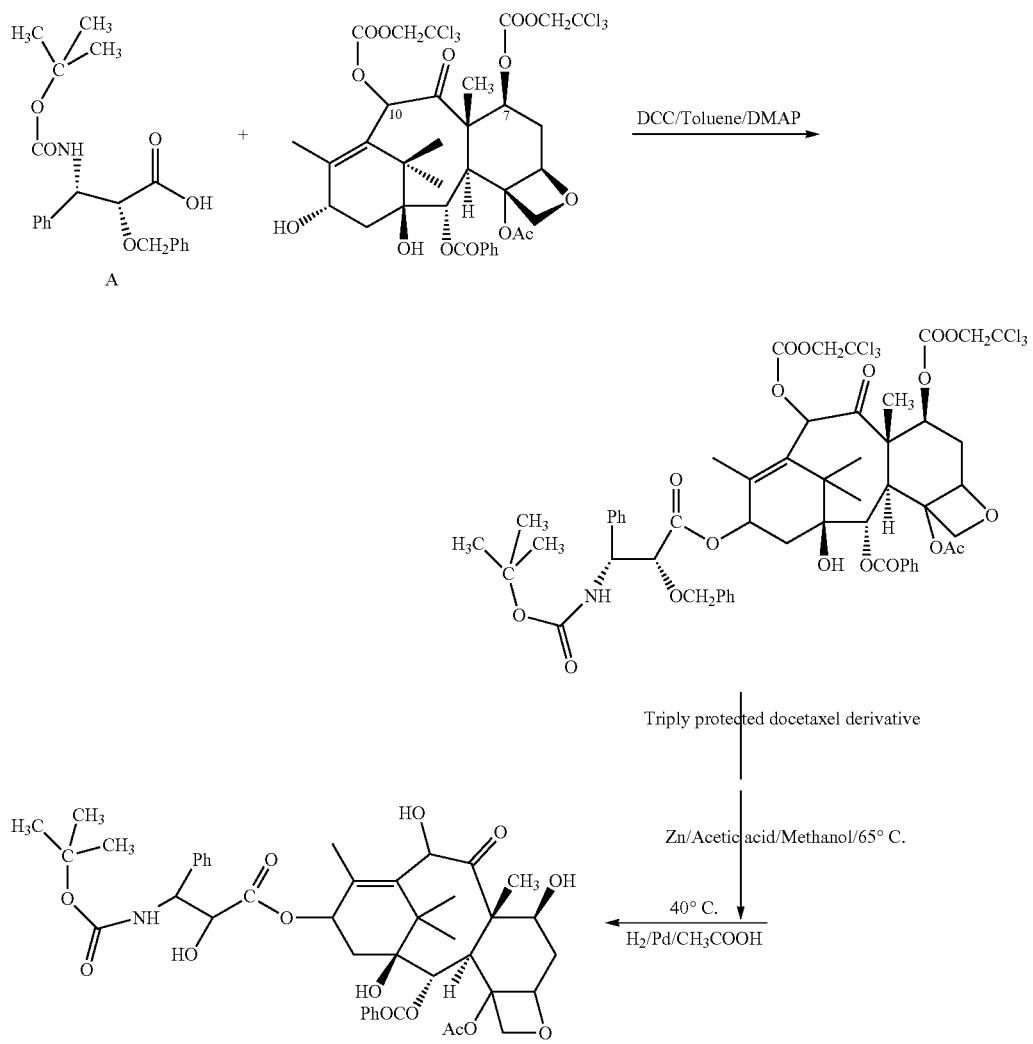

SUMMARY OF THE INVENTION

Particular aspects of the present specification relate to the process for preparing of docetaxel and its hydrate.

In one aspect, the present invention provides a process of preparation of (2R,3S)—N-carboxy-3-phenylisoserine, N-tert-butyl ester, 13-ester with 5(3)-20-epoxy-1,2(α),4,7(β),10(β),13(α)-hexa hydroxy tax-11-en-9-one 4-acetate 2-benzoate or docetaxel and its trihydrate (I)

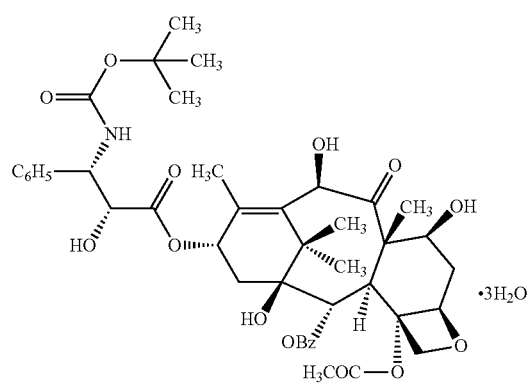

comprising the steps of—
a. selectively chloroacylating 7 and 10 hydroxy functions of 10-deacetyl baccatin III (or 10 DAB III) in halohydrocarbon solvent and pyridine to get (A);

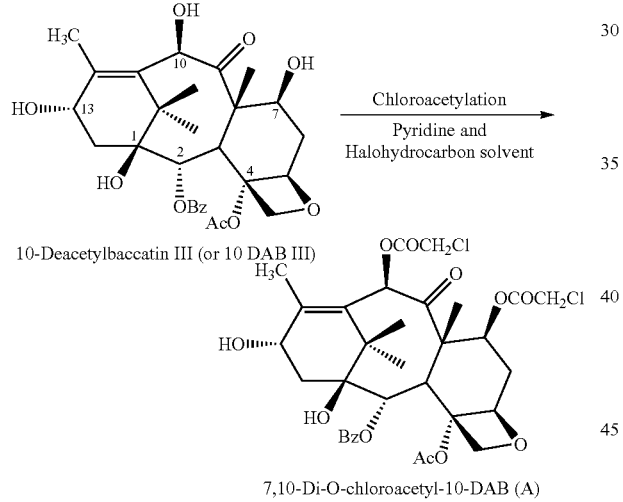

b. condensing (A) with benzyl protected side chain (B) in presence of a condensing agent and a moderator in an organic hydrocarbon solvent;

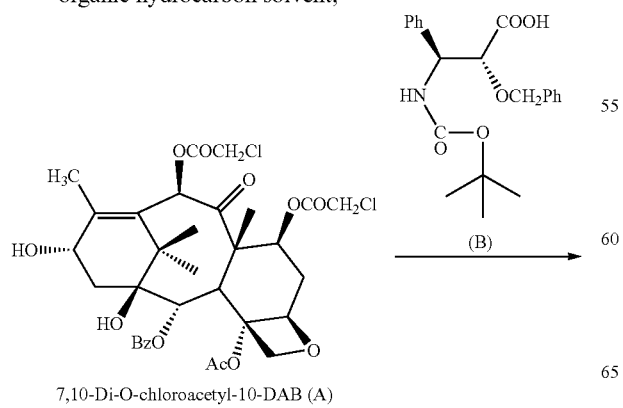

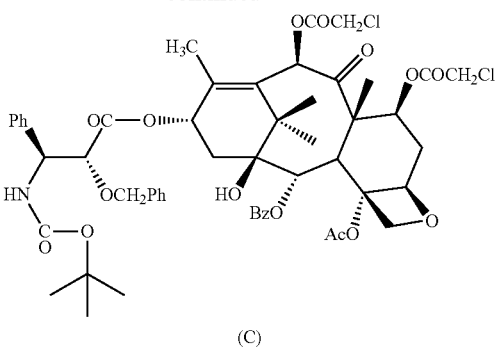

c. selective debenzoylation of side chain using a reducing agent in an organic solvent to get (D);

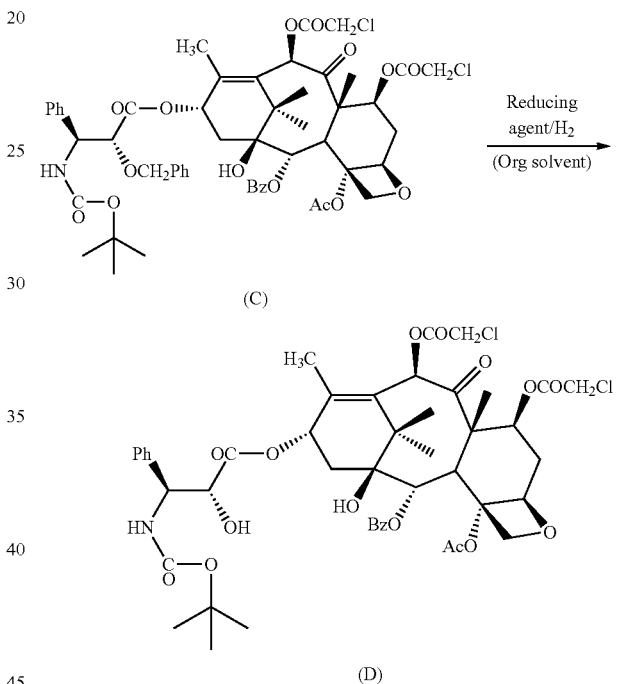

d. selectively deprotecting 7,10-di-O-chloroacyl group from (D) using a base to get docetaxel—

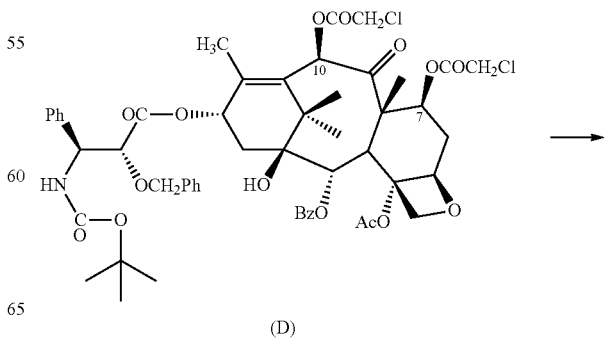

-continued

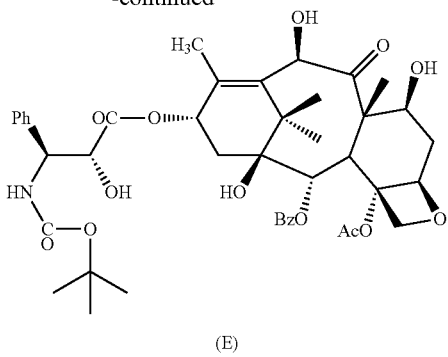

(E)

e. treating docetaxel (E) in the presence of organic solvents selective from—2-alkoxy ethanol or dimethyl sulphoxide and with water to get Docetaxel trihydrate.

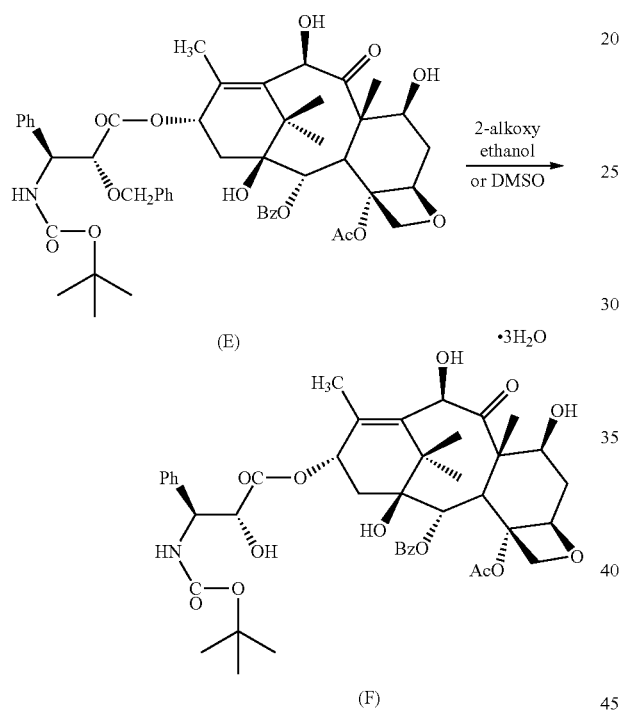

In another aspect, the present invention provides a process for purification of protected docetaxel i.e. Compound of formula-(D),

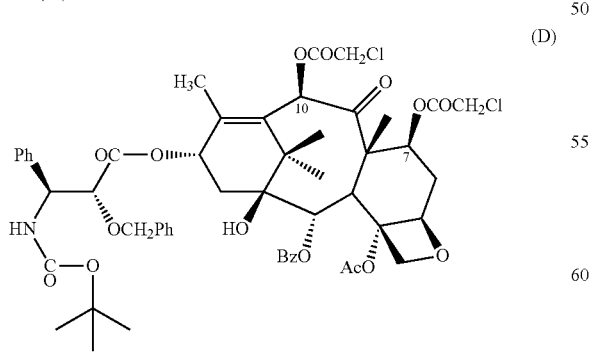

wherein the process comprising the steps of—
1. Column purification using hydrocarbon solvent and ester solvent in combination as eluents.
2. collecting and pooling the appropriate fractions
3. removing the solvents
4. add hydrocarbon solvent to the residue
5. isolate the pure Compound D
6. optionally drying the product at temperature ranging between 35 to 50° C. under vacuum.

In yet another aspect of the present invention, it provides a process of selectively deprotecting 7,10-di-O chloroacyl group from Intermediate-Compound D using a base

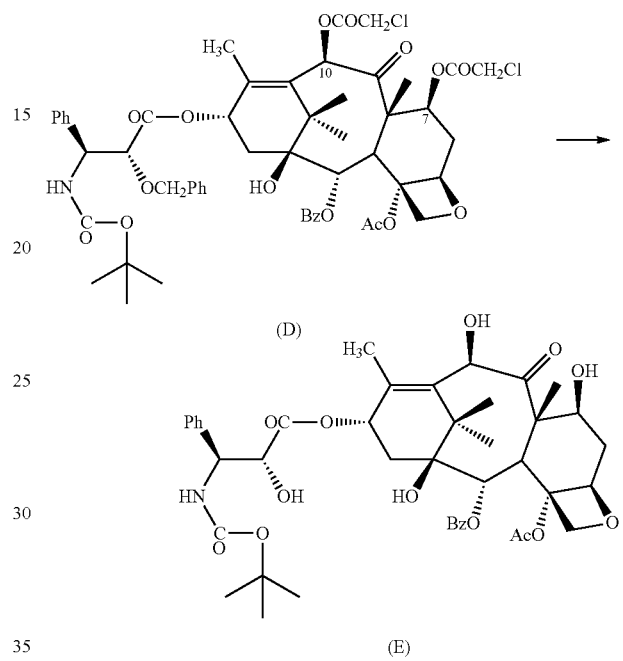

comprising the steps of—
a) providing solution of pyridine (solvent) and ammonia as base at temperature below 0° C.
b) add slowly Intermediate-Compound D maintaining temperature between −5 to +5° C.
c) mix cold water and ethyl acetate to the reaction mixture of step b)
d) maintain the pH of aqueous layer in the range of 2-4 using an acid.
e) separate the organic layer.
f) optionally re-extract the aqueous layer with of ethyl acetate.
g) combined the ethyl acetate layer
h) evaporate the ethyl acetate layer under vacuum to get docetaxel.
i) optionally dry the material at 40-55° C. under vacuum.

In further another aspect of the present invention, it provides a process for purification of Intermediate-Compound E comprising the steps of—
1. Column purification using hydrocarbon solvent and ester solvent in combination as eluents.
2. Collecting and pooling the appropriate fractions
3. removing the solvents
4. add hydrocarbon or nitrile solvent to the residue
5. isolate the pure Compound E
6. Optionally recrystallize with ketone and hydrocarbon solvent.

Other particular aspects of invention are discussed in the detailed description of the present invention.

DETAILED DESCRIPTION OF THE INVENTION

As set forth herein, aspects of the present invention relate to the process for preparation of docetaxel and its trihydrate (I).

In one embodiment of the present application, it provides a process of preparation of (2R,3S)—N-carboxy-3-phenylisoserine, N-tert-butyl ester, 13-ester with 5(β)-20-epoxy-1,2(α), 4,7(β),10(β),13(α)-hexa hydroxy tax-11-en-9-one 4-acetate 2-benzoate or docetaxel and its trihydrate (I)

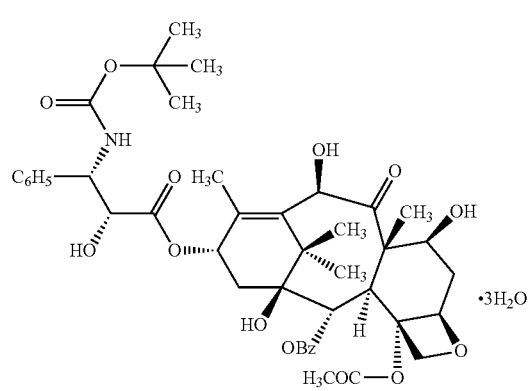

comprising the steps of—
a. selectively chloroacylating 7 and 10 hydroxy functions of 10-deacetyl baccatin III (or 10 DAB III) in halohydrocarbon solvent and pyridine to get (A);

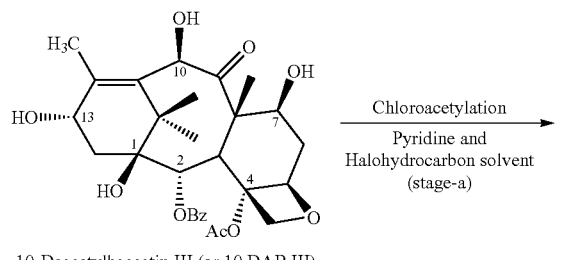

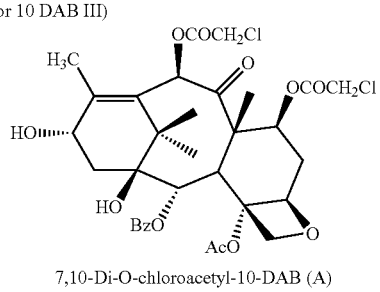

Selectively chloroacylating 7 and 10 hydroxy functions of 10-deacetyl baccatin III is one of the peculiar aspect of the present invention, which particularly involves the use of chloroacetyl group as hydroxy protecting function and provides a specific effect to reaction kinetics, while the esterification is carried out with a open chain side chain.

10-Deacetyl baccatin is reacted with chloro acetyl chloride at temperature ranging between −10 to 10° C. In one the preferred aspect of the invention, it involves 0-5° C. temperature as preferred temperature.

The reaction is carried out using halohydrocarbon solvent, selected from dihalo or trihalo substituted hydrocarbon solvent. Preferably, dichloro methane as solvent was used among the solvent of choice.

The reaction of chloroacetylation also involved use of catalyst like pyridine and co-catalyst like 4,4-dimethylaminopyridine (DMAP). 7,10-di-O-chloroacetyl-10-DAB (Compound of formula A) obtained after reaction is crystallized and dried to get white to off white product. The process of crystallization and drying for the Compound of formula A involved the conventional processes, which are not limited to evaporation, solvent-anti-solvent methods and the like.

b. Condensing compound of formula (A) with benzyl protected side chain (B) in presence of a condensing agent and a moderator in an organic hydrocarbon solvent;

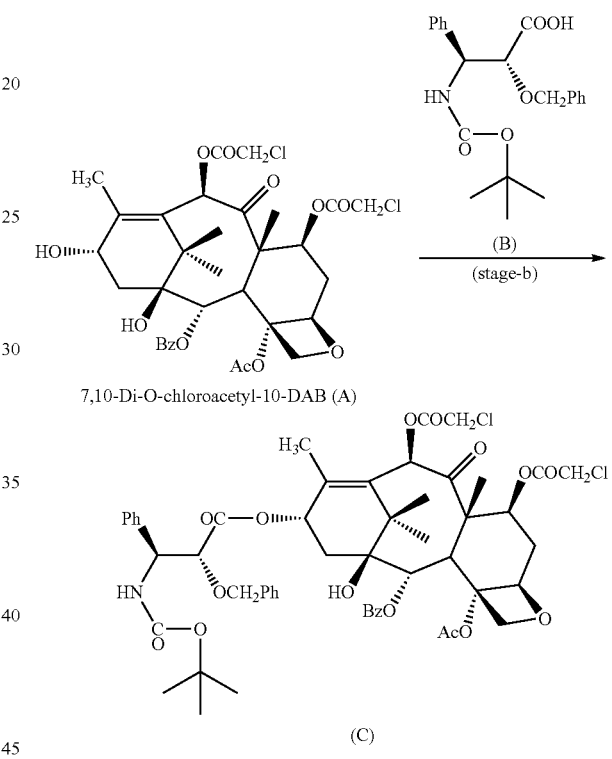

Condensing compound of formula (A) with benzyl protected side chain (B) step is also known as esterification, wherein hydroxy group at C-13 of taxane ring form an ester with carboxylic acid group of benzyl protected open chain side chain (Compound B).

It has been observed by the inventors of the present application that chloroacetyl protecting group serves important role of maximizing the esterification reaction in a shorter durations in comparisons of other protecting groups. Often this magnitude of reaction kinetics remained upto more than 2-3 folds in comparison to the other well known protecting groups like Trocc, TES etc.

7,10-di-O-chloroacetyl-10-DAB [or Compound of formula-(A)] is coupled with 2'-O-Benzyl-N—BOC-phenylisoserine [or Compound of formula-(B)] in presence of a condensing agent, which are selected from, but are not limited to N,N-Diisopropyl Carbodiimide (DIPC) or Dicyclohexyl Carbodiimide (DCC) or N-hydroxy succinimide (NHS) or the like and catalystic moderator selected from 4-dimethyl amino pyridine (DMAP) or Hydroxy benzotriazole (HOBt). Organic hydrocarbon solvent utilized in the reaction may be selected from toluene or xylene or benzene, however, in a particular embodiment, preferred solvent of the reaction was aromatic hydrocarbon solvent like toluene.

Reaction temperature for the esterification reaction is one of the particularly important aspect of the reaction and more preferably the reaction is carried out at less than 20° C. In one of the preferred embodiment, the reaction temperature remained in the range of 10-20° C. to get the esterified product as 7,10-Di-O-chloroacetyl-2'-O-Benzyl docetaxel [or Compound of formula-(C)].

The coupled crude product may be optionally purified on column using silica gel and ethyl acetate in addition of hexane as solvent system, which may be followed by crystallization to get pure product.

c. selective debenzylation of side chain using a reducing agent in an organic solvent to get (D);

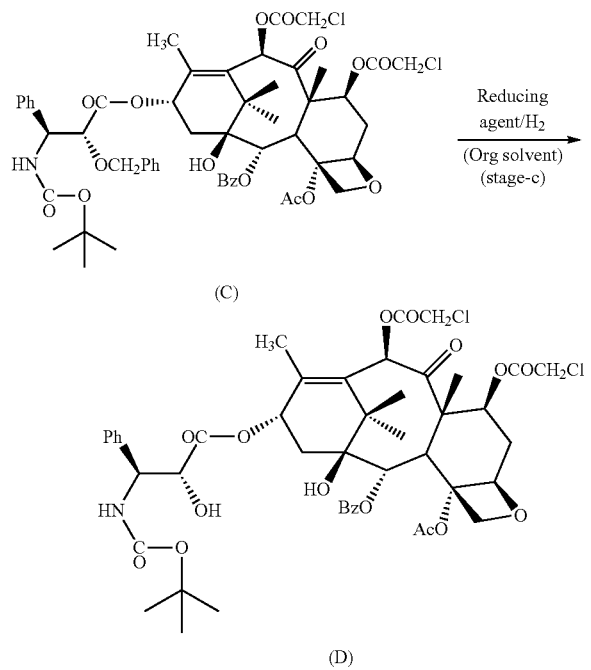

In this step of selective debenzylation of side chain of compound of formula (C), it involves catalytic hydrogenation to selectively debenzylate the side chain.

Compound of formula (C) i.e. 7,10-Di-O-chloroacetyl-2'-O-Benzyl docetaxel on hydrogenation in the presence of a reducing agent selected from Pd on Charcoal, Rh or Ni resulted in the product as Compound of formula (D). In a particular embodiment, Pd/C was used as reducing agent.

Organic solvent utilized in this step may be selected from but are not limited to tetrahydrofuran (THF) or THF-ethanol mixture or THF, Ethanol and water mixture or DMF or Ethyl acetate.

During hydrogenation reaction, the reaction medium pH is often maintained between 2-5 using an acid that may be selected from organic or inorganic acid.

In the autoclave or similar sealed reactor, hydrogen gas pressure is maintained ranging between 45 PSI to about 90 PSI, as long as TLC confirms the consumption of compound of formula (C).

Filter the reaction mass after reaction completion through celite bed and adjust the pH to neutral with sodium bicarbonate. The solvent is recovered under vacuum usually between 40-60° C. to get the viscous liquid. The product as compound of formula (D) is isolated by conventional methods.

Optionally compound of formula (D) may be purified on silica gel (230-400 mesh) column under nitrogen pressure (0.1-1.0 kg) using n-Hexane and ethyl acetate as an eluents composition. The collected appropriate fraction may be pooled together and subjected to concentration at 35-50° C. under vacuum to get the viscous semisolid. Addition of antisolvent like n-Hexane to the residue and cool between 05-20° C. is one of the preferable step to isolate the crystalline solid product. The solid material as purified compound of formula (D) is isolated by conventional means and optionally dried at 40-50° C. under vacuum for 3-4 hours.

d. Selectively deprotecting 7,10-di-O-chloroacyl group from (D) using a base to get docetaxel—

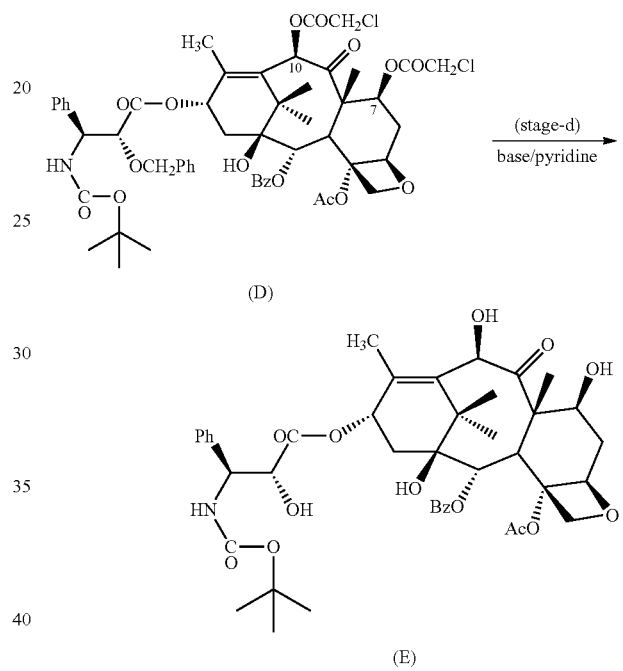

Selectively deprotecting 7,10-di-O-chloroacyl groups from compound of formula (D) is also one of the preferred embodiment of the present invention, which comprise the use of a base selected from but are not limited to ammonia or pyridine or mixture thereof.

The reaction is carried out at a lower temperature ranging between −10 to 10° C. In one of the embodiment, said temperature was maintained between −5 to 5° C. for a time duration between 2-6 hours.

Often the reaction kinetics was monitored by HPLC. Once the reaction is completed, ice cold water and an ester solvent selected from ethyl acetate or propyl acetate is added to the reaction mixture.

In this heterogeneous mixture phases, it is preferable to maintain the pH of aqueous layer in the range of 2-5. An inorganic acid like hydrochloric acid or sulphuric acid may be used for maintaining this pH.

The temperature is also crucial and it should be preferred that the temperature should also not increase above 10° C. in order to avoid process, isomeric or degradative impurities formation.

Organic layer containing the ester solvent is separated along with other repeated extractions of the aqueous layer from the same solvent.

All the ethyl acetate layers were pooled and washed and the material as compound of formula (E) is isolated by conventional methods known to the person skilled in the art, which include the solvent recovery and drying the product under vacuum.

In one of the particular embodiment, the material was dried at 45-50° C. under vacuum for about 4-6 hours to get Docetaxel (E).

Often it is preferred to carry out the optional purification for docetaxel or Intermediate Compound E, which comprise the following steps—
1. Column purification using hydrocarbon solvent and ester solvent in combination as eluents.
2. collecting and pooling the appropriate fractions
3. removing the solvents
4. add hydrocarbon or nitrile solvent to the residue
5. isolate the Compound E
6. optionally recrystallize with ketone and hydrocarbon solvent.

This purification may be repeated as per the need of the isolated Compound (E), since complying with the ICH guidelines is one aspect, which may be met easily by the process of this present invention. A pure docetaxel having a purity of more than 99.5% w/w may be obtainable in the anhydrous form in this stage.

e. treating docetaxel (E) in the presence of organic solvents selective from –2-alkoxy ethanol or dimethyl sulphoxide and with water to get docetaxel trihydrate.

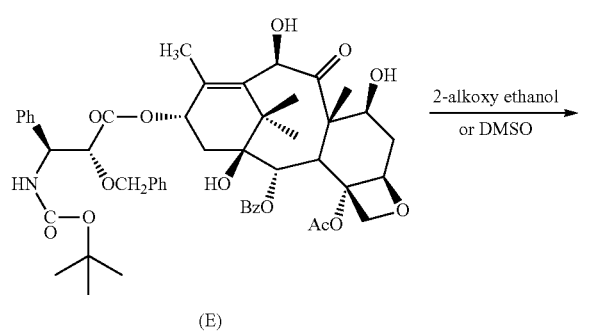

(E)

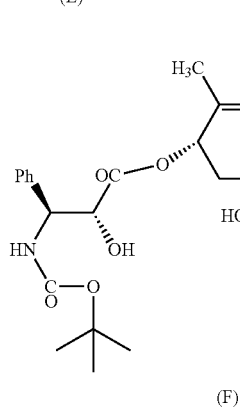

(F)

Treatment of docetaxel (E) for the purpose of preparing its hydrate comprising the steps of combining the docetaxel (E) with an organic solvent selected from alkoxy alcohol or dimethylsulphoxide.

In particular embodiment of the present invention, the process comprises combining anhydrous docetaxel or Compound of formula (E) and 2-methoxy ethanol. Reaction mass was stirred to dissolve completely at room temperature. Cooled this reaction mass is essential upto a range of temperature between 5-20° C. Preferably, this temperature may be between 10-15° C.

Water is added to initiate the hydration and is added slowly in 1-4 hrs at 10-15° C. The temperature after water addition may be maintained between 4-10 hours and preferably between 5-7 hrs.

Isolation of the hydrate of docetaxel may be performed by convention methods know to the person skilled in the art, which includes but are not limited to Filtration, washing and drying. The product as hydrate may be any hydrate including monohydrate, dehydrate, trihydrate or mixture thereof. Often the process of the present invention provides a hydrate, which contains predominately a trihydrate having water content ranging between 5-7%. The product may be air dried suitably in order to get MC between 5-7%.

In another embodiment of the present application, it provides a process of purification of protected docetaxel i.e. Compound of formula-(D),

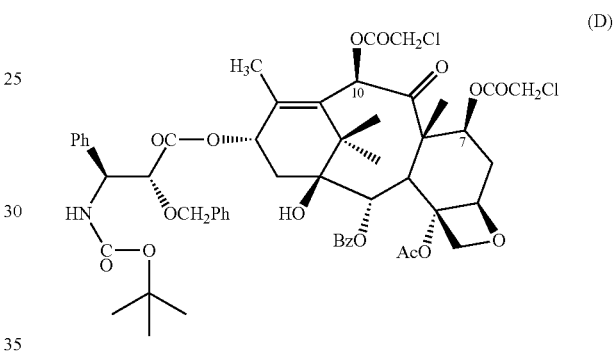

wherein the process comprising the steps of—
1. column purification using hydrocarbon solvent and ester solvent in combination as eluents.
2. collecting and pooling the appropriate fractions
3. removing the solvents
4. add hydrocarbon solvent to the residue
5. isolate the pure Compound D
6. optionally drying the product at temperature ranging between 35 to 50° C. under vacuum.

The specifics of this process of purification of protected docetaxel i.e. Compound of formula-(D) are given in the example, which may not be construed to be limiting the scope of the invention.

In yet another embodiment of the present application, it provides a process of selectively deprotecting 7,10-di-O chloroacyl group from Intermediate-Compound D using a base

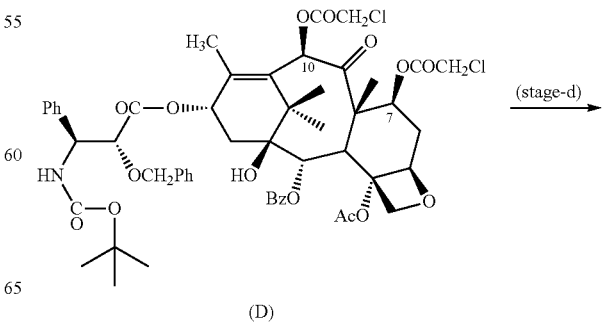

(D)

-continued

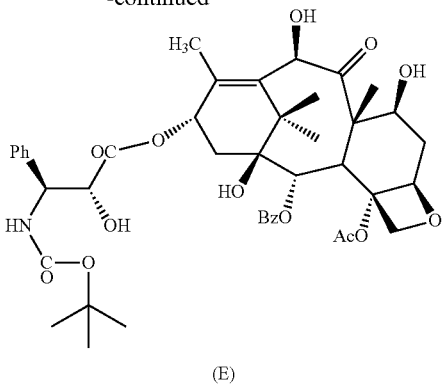

(E)

comprising the steps of—
- a) providing solution of pyridine (solvent) and ammonia as base at temperature below 0° C.
- b) add slowly Intermediate-Compound D maintaining temperature between −5 to +5° C.
- c) mix cold water and ethyl acetate to the reaction mixture of step b)
- d) maintain the pH of aqueous layer in the range of 2-4 using an acid.
- e) separate the organic layer.
- f) optionally re-extract the aqueous layer with of ethyl acetate.
- g) combined the ethyl acetate layer
- h) evaporate the ethyl acetate layer under vacuum to get docetaxel.
- i) optionally dry the material at 40-55° C. under vacuum.

The specifics of this process of selectively deprotecting 7,10-di-O chloroacyl group from Intermediate-Compound D using a base are given in the example section, which may not be construed to be limiting the scope of the invention.

In further embodiment of the present application, it provides a process of purification of Intermediate-Compound E comprising the steps of—
1. column purification using hydrocarbon solvent and ester solvent in combination as eluents.
2. collecting and pooling the appropriate fractions
3. removing the solvents
4. add hydrocarbon or nitrile solvent to the residue
5. isolate the pure Compound E
6. optionally recrystallize with ketone and hydrocarbon solvent.

The specifics of this process of purification of protected docetaxel i.e. Compound of formula-(E) are given in the example, which may not be construed to be limiting the scope of the invention.

The details of the process are delineated in the scheme-1 and their specifics demonstrated in the example may not be construed to limit the scope of the present invention.

Scheme-I: Preparation of DOCETAXEL TRIHYDRATE as Per the Present Invention

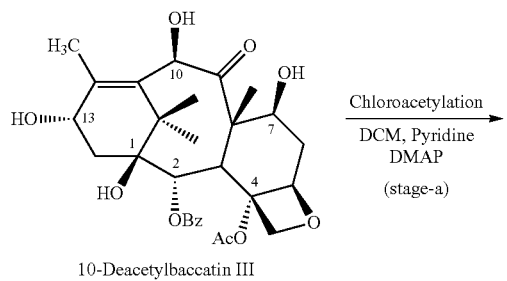

10-Deacetylbaccatin III

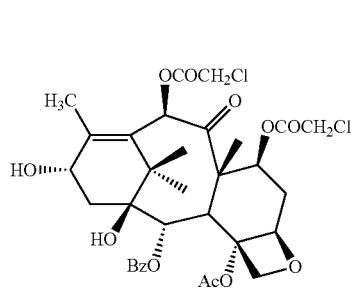

(A)

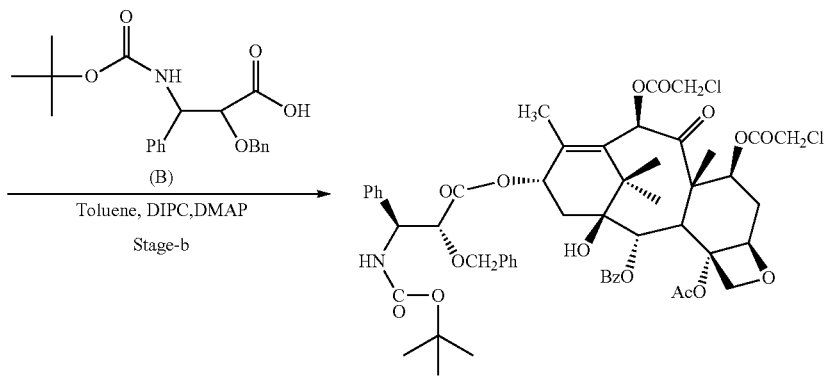

(C)

Stage-c | Pd/C, H₂ Gas
THF: Ethanol (1:1)

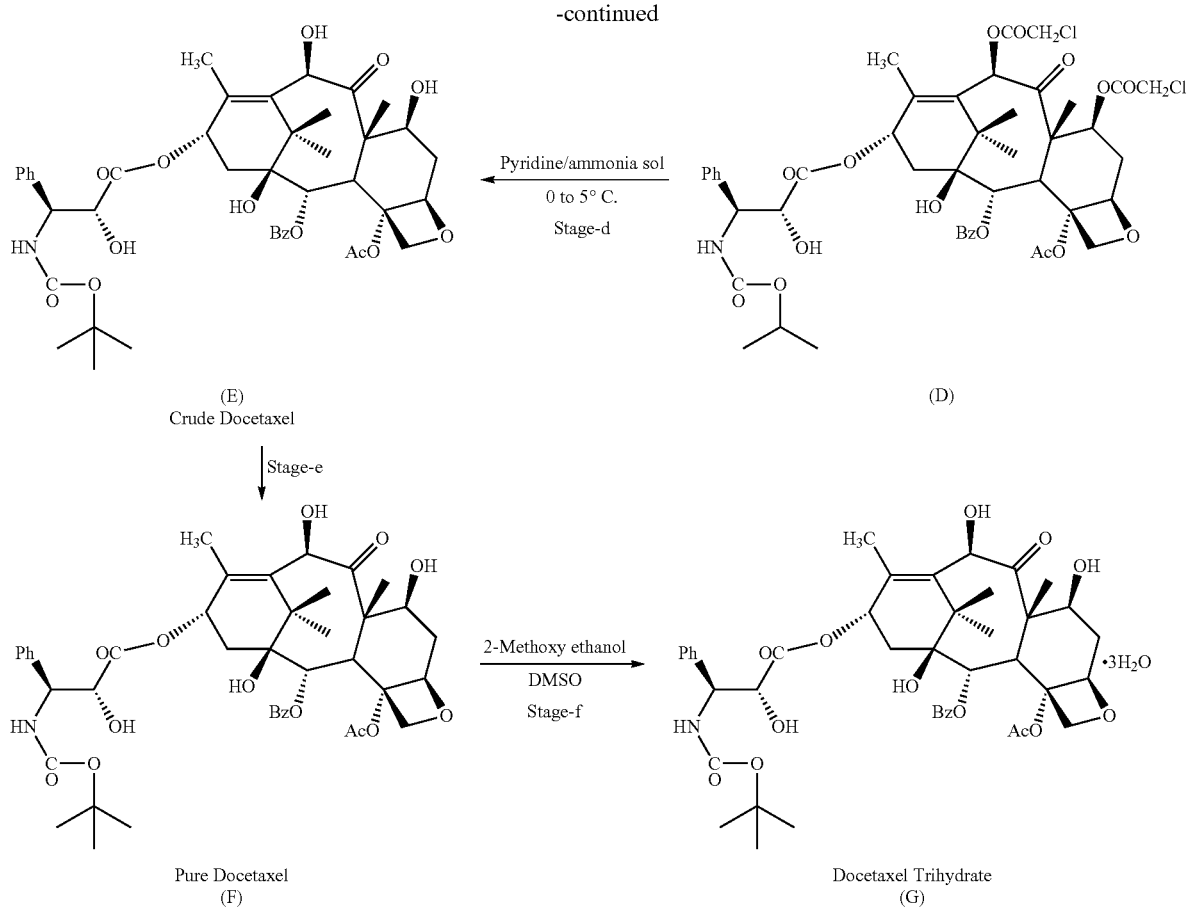

(E) Crude Docetaxel (D)

Pure Docetaxel (F)

Docetaxel Trihydrate (G)

All percentages and ratios used herein are by weight of the total composition and all measurements made are at about 25° C. and about normal pressure, unless otherwise designated. All temperatures are in degrees Celsius unless specified otherwise. As used herein, "comprising" (open ended) means the elements recited, or their equivalent in structure or function, plus any other element or elements which are not recited. The terms "having" and "including" are also to be construed as open ended. As used herein, "consisting essentially of" means that the invention may include ingredients in addition to those recited in the claim, but only if the additional ingredients do not materially alter the basic and novel characteristics of the claimed invention. All ranges recited herein include the endpoints, including those that recite a range "between" two values. Whether so indicated or not, all values recited herein are approximate as defined by the circumstances, including the degree of expected experimental error, technique error, and instrument error for a given technique used to measure a value.

In another embodiment, docetaxel or its hydrate including docetaxel trihydrate obtained by the process of the present application may be formulated as solid compositions for oral administration in the form of capsules, tablets, pills, powders or granules. In these compositions, the active product is mixed with one or more pharmaceutically acceptable excipients. The drug substance can be formulated as liquid compositions for oral administration including solutions, suspensions, syrups, elixirs and emulsions, containing solvents or vehicles such as water, sorbitol, glycerine, propylene glycol or liquid paraffin.

The compositions for parenteral administration can be suspensions, emulsions or aqueous or non-aqueous sterile solutions. As a solvent or vehicle, propylene glycol, polyethylene glycol, vegetable oils, especially olive oil, and injectable organic esters, e.g. ethyl oleate, may be employed. These compositions can contain adjuvants, especially wetting, emulsifying and dispersing agents. The sterilization may be carried out in several ways, e.g. using a bacteriological filter, by incorporating sterilizing agents in the composition, by irradiation or by heating. They may be prepared in the form of sterile compositions, which can be dissolved at the time of use in sterile water or any other sterile injectable medium.

Pharmaceutically acceptable excipients used in the compositions comprising docetaxel or docetaxel trihydrate of the present application include, but are but not limited to diluents such as starch, pregelatinized starch, lactose, powdered cellulose, microcrystalline cellulose, dicalcium phosphate, tricalcium phosphate, mannitol, sorbitol, sugar and the like; binders such as acacia, guar gum, tragacanth, gelatin, pregelatinized starch and the like; disintegrants such as starch, sodium starch glycolate, pregelatinized starch, Croscarmellose sodium, colloidal silicon dioxide and the like; lubricants such as stearic acid, magnesium stearate, zinc stearate and the like; glidants such as colloidal silicon dioxide and the like; solubility or wetting enhancers such as anionic or cationic or neutral surfactants, waxes and the like. Other pharmaceutically acceptable excipients that are of use include but not limited to film formers, plasticizers, colorants, flavoring agents, sweeteners, viscosity enhancers, preservatives, antioxidants and the like.

Pharmaceutically acceptable excipients used in the compositions of docetaxel or docetaxel trihydrate of the present application may also comprise to include the pharmaceutically acceptable carrier used for the preparation of solid dispersion, wherever utilized in the desired dosage form preparation.

Certain specific aspects and embodiments of the present application will be explained in more detail with reference to the following examples, which are provided by way of illustration only and should not be construed as limiting the scope of the invention in any manner.

EXAMPLES

Example-01

Process of Preparation of Docetaxel

The process of preparation of docetaxel comprises of following four stages, namely a to d. Individual stages are provided separately herein below.

Stage a). Preparation of
7,10-Di-O-Chloroacetyl-10-DAB (A)

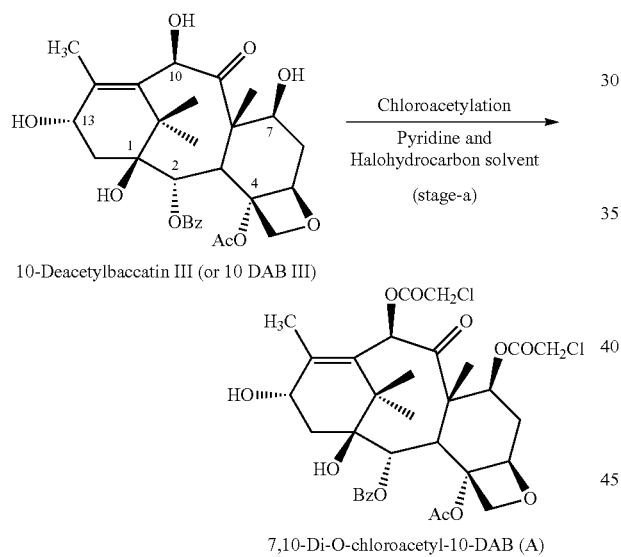

Charge 7.5 liter of dichloromethane and 1.0 liter of pyridine in to a clean RB flask under stirring at room temperature. Then add 500 gram 10-DAB under stirring under nitrogen atmosphere. Then cool the reaction mixture to −5 to 0° C. Add 22.42 gm N,N-di-methyl amino pyridine under stirring. Add chloroacetyl chloride solution (Prepared using 384.3 g chloroacetyl chloride in 5.0 L dichloromethane) maintaining reaction temperature −5 to 5° C. in 1.5 hours under stirring. Add remaining 11.21 gm of N,N-di-methyl amino pyridine after half addition of chloroacetyl chloride solution and stir for 30 minutes after completion of addition (Monitor the reaction by HPLC). Mixed 10 liter of DM water with 800 ml hydrochloric acid and added to reaction mass under stirring. (pH of aqueous layer should be in the range of 2-4) and stir for 30 minutes. Separate the organic layer and wash with DM water (2×7.5 L) [pH of aqueous layer should be neutral]. Dissolved 250 g sodium bicarbonate in 5 liter of DM water and added to the organic layer and stir for 30 minutes. Separate the organic layer. Wash the organic layer with 5.0 liter of DM Water. Make the organic layer moisture free by addition of 2.0 kg anhydrous sodium sulfate. Recover the organic layer at 40-50° C. under vacuum to get the viscous mass. Added 5.0 liter toluene to the viscous mass under stirring and cool to 10° C. Filter the solid material (Discard the filtrate). Added 13 liter of n-Hexane to the solid material and stir for 30 minutes. Filter the separated solid material, wash with 1 liter of n-Hexane. Dry the solid product (A) at 60° C. under vacuum till achieves the moisture limit.

Stage b). Preparation of
7,10-di-O-chloroacetyl-2'-O-benzyl docetaxel (C)

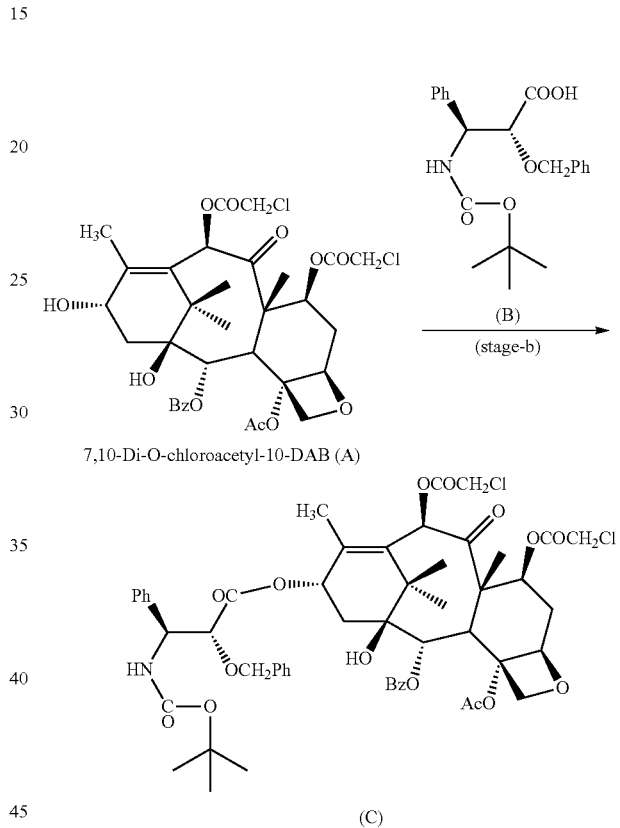

To a clean and dry RB flask charge 2.25 liter of toluene. Cool to 8-10° C. and add 300 gm of (A) and Benzyl protected Phenyl Iso-serine side-chain (B) 207.4 gm and 10.5 gm of N,N-di-methyl amino pyridine under stirring. Add 108.5 gm of N,N-Diisopropyl carbodiimide and continued the stirring for 24 hours at 10-20° C. Monitor the reaction by HPLC. After completion of reaction added 4.5 liter of ethyl acetate to the reaction mass and stir for 5 minutes. Filter the reaction mass on a buchner funnel under vacuum and collect the filtrate. Dissolved 300 gm of ammonium chloride in 2.0 liter of DM water and added to the filtrate under stirring and stir for 5 minutes. Separate the organic layer and give the sodium bicarbonate washing (sodium bicarbonate 150.0 g dissolved in DM water 2.0 L) and brine washing (sodium chloride 500 g in 3 L DM water) under stirring for 5 minutes. Make the organic layer moisture free. Recover the organic layer at 55-65° C. under vacuum up to dryness. Remove the material (C) from RB flask and dry at 55-65° C. under vacuum for 4-5 hours till achieved the LOD limit.

Stage c). Preparation of 7,10-Di-O-Chloroacetyl-Docetaxel (D)

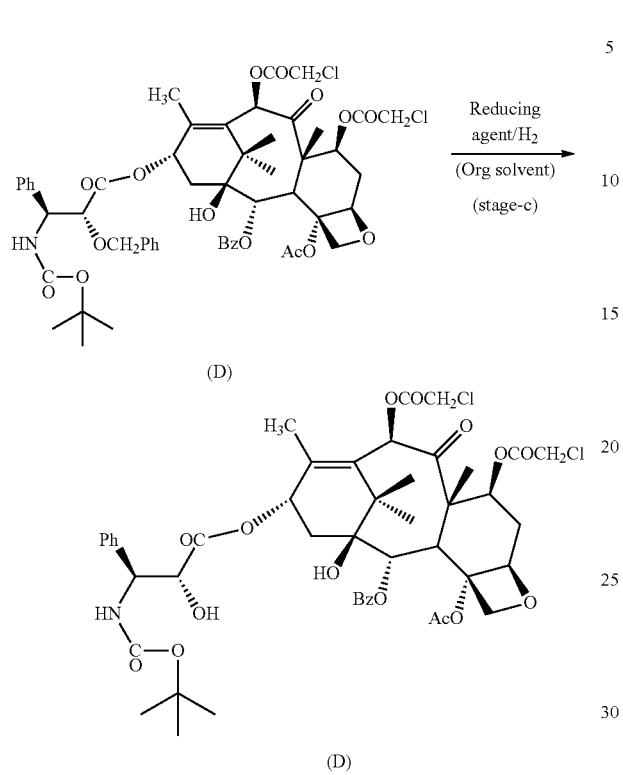

To a clean and dry Autoclave charge 130.0 gm of (C) and 650 ml of tetrahydrofuran. Add 650 ml of ethanol, 65 ml of DM Water and 6.5 gm of Pd/C (5%) and maintain the pH (2-4) by addition of hydrochloric acid and stir for one hour. Filter the content through 0.5 micron filter paper. Add 26 gm of Pd/C to the filtrate and maintain pH (2-4). Charge the suspension to autoclave, start the stirring and applied 75 psi hydrogen gas pressure for 30-60 hours. Completion of reaction is checked by TLC. Released the hydrogen gas and purged the solution with nitrogen gas. Filter the reaction mass through celite bed and adjust the pH to neutral with sodium bicarbonate. Recover the solvent at 50-55° C. under vacuum to get the viscous liquid. Then added 2.0 liter of DM water and extracted the reaction mixture with ethyl acetate (3×2 L). Combined the ethyl acetate layer and wash with 2 liter of DM water (pH of aqueous layer should be neutral) and brine solution (390 gm dissolved in 2 liter DM water). Make the organic layer moisture free by addition of 500 gm anhydrous sodium sulphate. Recover the ethyl acetate layer at 50-55° C. under vacuum to get the viscous semi solid. Purify the material (D) with silica gel (230-400 mesh) under nitrogen pressure (0.5-1.0 kg) using n-Hexane and ethyl acetate as an eluent. Mix the appropriate fraction and concentrate at 40-50° C. under vacuum to get the viscous semisolid. Add 1.5 liter of n-Hexane to the residue and cool to 10-20° C. under stirring and maintain this temperature for one hour. Filter the solid material, wash with 500 ml of n-Hexane. Dry the product at 40-50° C. under vacuum for 3-4 hours.

Stage d). Preparation of Crude Docetaxel (E)

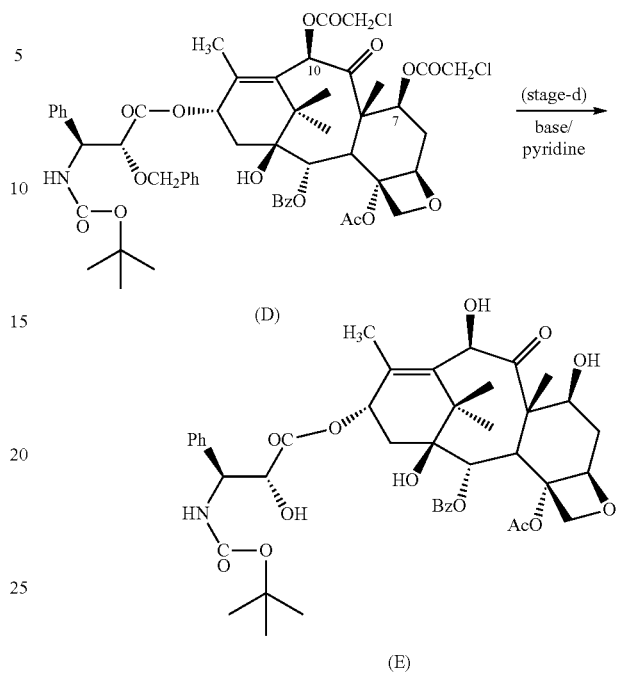

To a clean and dry flask charge 1.6 liter of pyridine and cool up to 0° C. under stirring. Charge 400 ml ammonia solution and cool it again −5° C. Charge 200 gm of (D) under stirring and maintain temperature −5 to 5° C. for 4-5 hours. Monitor the reaction by HPLC. Add 3.0 liter ice cold water and 4.0 liter of ethyl acetate to the reaction mixture and maintain the pH of aqueous layer (pH should be in the range of 2-4) by addition of hydrochloric acid under stirring. The temperature should not increase 10° C. Separate the organic layer. Again extracted the aqueous layer with 3.0 liter of ethyl acetate. Combined the ethyl acetate layer and wash with 3.0 liter of DM water and sodium bicarbonate solution (200 gm dissolved in DM water of 3.0 L). Make the ethyl acetate layer moisture free by addition of 1.5 kg anhydrous sodium sulfate. Recover the ethyl acetate layer at 50-55° C. under vacuum to get the solid product. Dry the material at 50° C. under vacuum for 4-6 hours to get Docetaxel crude~160 gm (E).

Example-02

Process of Purification for Crude Anhydrous Docetaxel (E)

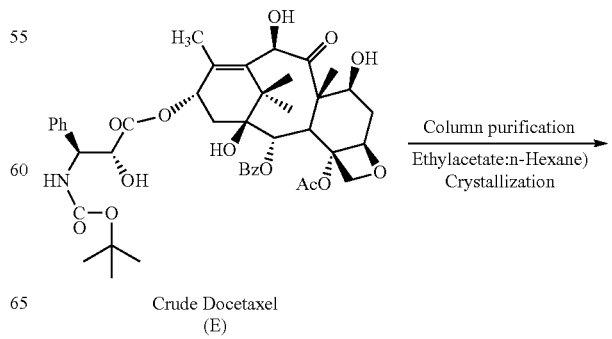

Crude Docetaxel (E)

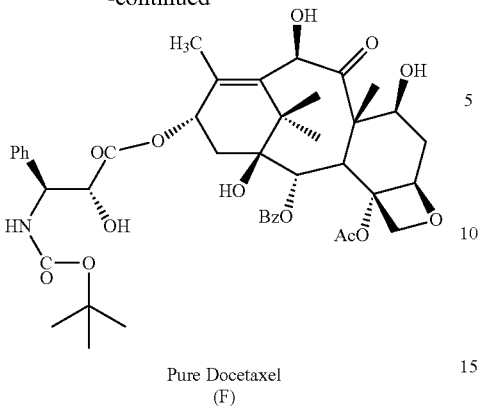

Pure Docetaxel
(F)

To a clean and dry flask charge Docetaxel crude (160 gram) in dichloromethane (1.6 L) and added silica gel (230-400 mesh, 320 gram) and concentrate the suspension at reduced pressure at 40-50° C.
till mass become free flowing in nature. Pack 2.88 kg silica gel (230-400 mesh) in glass column with sintered G-2 base with solvent system (Ethyl acetate:n-Hexane, 2:1). Run the above solvent system in the glass column under N2 pressure (0.5-1.0 kg/cm2) @250-500 ml per minute. Collect the fraction 1 L each. Discard the fractions containing impurities as monitored on TLC.

Collect and mix the pure fraction and concentrate at reduce pressure at 45-55° C. to get the viscous semi solid product Add acetonitrile (1.5 L) and further distilled ~700-800 ml solvent. Cooled the mixture at 5-10° C.
under stirring for one hour. Filter the separated solid material, wash with acetonitrile (150 ml) to get the product. (~120 gram)

The above material was dissolved in Acetone (4.2 L) at 20-25° C. under stirring. To this solution was added n-Hexane (11.2 L) at 20-25° C. under stirring and maintain this temperature for 4-5 hours to get the crystallized product. Filter the product and wash with n-Hexane (0.7 L×2). Dry the material at 40-50° C. under vacuum for 12-16 hours to get the anhydrous Docetaxel Example-03

Process for Selective De-Protection of 7,10-Di-O-Chloroacetyl Group of Intermediate Compound (D)

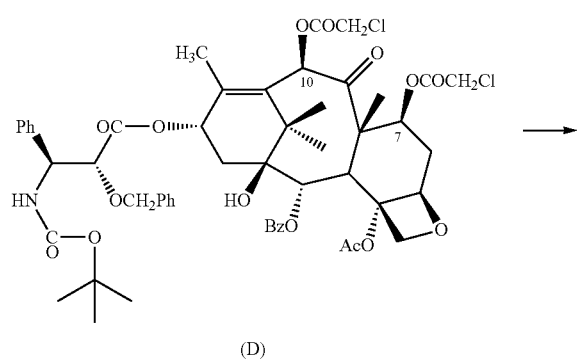

(D)

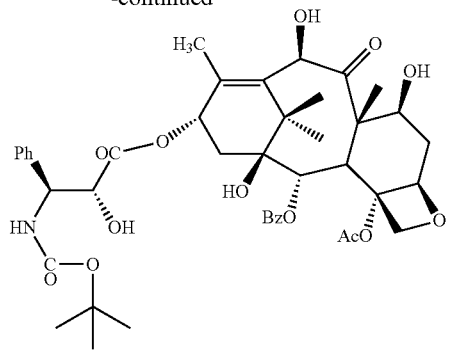

(E)

To a clean and dry flask charge 0.8 liter of pyridine and cool up to −5° C. under stirring. Charge 200 ml ammonia solution and cool it again −5° C. Charge 100 gm of (D) under stirring and maintain temperature −5 to 5° C. for 4-5 hours. Monitor the reaction by HPLC. Add 1.5 liter ice cold water and 2.0 liter of ethyl acetate to the reaction mixture and maintain the pH of aqueous layer (pH should be in the range of 2-4) by addition of hydrochloric acid under stirring. The temperature should not increase 10° C. Separate the organic layer. Re-extracted the aqueous layer with 1.5 lit of ethyl acetate. Combined the ethyl acetate layer and wash with 1.5 lit of DM water and sodium bicarbonate solution (100 gm dissolved in DM water of 1.6 L). Make the ethyl acetate layer moisture free by addition of 0.75 kg anhydrous sodium sulfate. Recover the ethyl acetate layer at 45-50° C. under vacuum to get the solid crystalline product. The material was dried at 50° C. under vacuum for 4-6 hours to get Docetaxel (E) crude~84 gm.

Example-04

Process for the Purification of 7,10-Di-O-Chloroacetyl-Docetaxel (D)

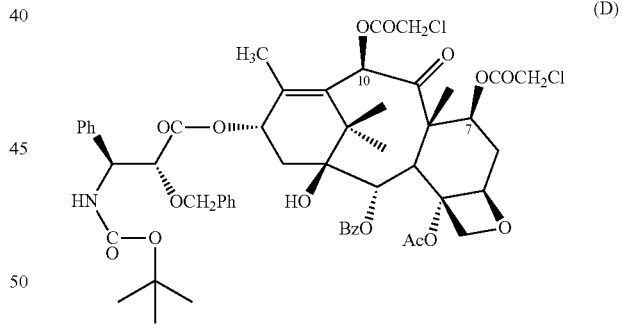

(D)

Dissolved the 7,10-Di-O-Chloroacetyl-Docetaxel (175 g) in dichloromethane (1.75 L) and added silica gel (230-400 mesh) and concentrate at reduced pressure at 40-50° C. up to dryness to get the free flowing in nature. Load the precoated material in glass column packed with 3.85 kg silica gel (230-400) in ethyl acetate: n-Hexane, 1:2 system. Run the column under nitrogen pressure (0.5-1.0 kg) and collect the fraction of 1.00 L each up To 40 L. Monitor the elution of product and impurities on TLC. Collect and mix the pure fraction and concentrate at 40-50° C. under vacuum to get the viscous semi solid. Add absolute ethanol (1.2 L) and cool the content to 15-20° C. and then added n-hexane (4.2 L) under stirring and further cool to 10-15° C. under stirring for 3-4 hours. Filter the crystallized mass and wash with n-hexane (1.0 L). dry the product at 40-50° C. under vacuum for 3-4 hours.

Example-05

Preparation of Docetaxel trihydrate (G) by Using the Solvent 2-Methoxy Ethanol

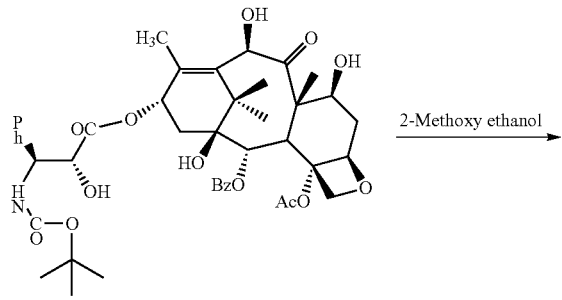

Pure Docetaxel (F)

2-Methoxy ethanol →

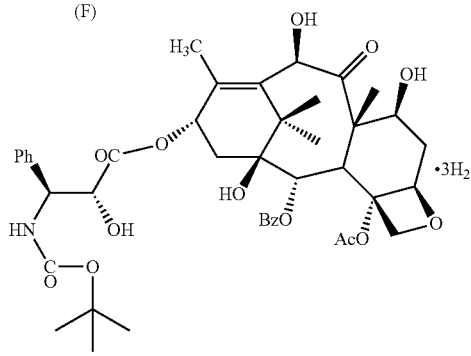

Docetaxel Trihydrate (G)

Charged 4.0 gm of anhydrous docetaxel and 66.4 ml of 2-methoxy ethanol into a round bottom flask. Stirred the reaction mass to dissolve completely at room temperature. Cooled the reaction mass to 10-15° C. and start addition of 664 ml of water slowly in 1-2 hrs at 10-15° C. Maintain the temperature for 6 hrs. Filter the mass and suck dried. Then washed with water, air dried the material to get MC between 5-7%

Example-06

Preparation of Docetaxel trihydrate (G) by Using the Solvent DMSO

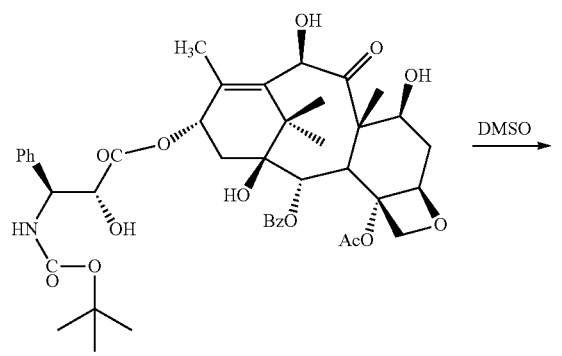

Pure Docetaxel (F)

DMSO →

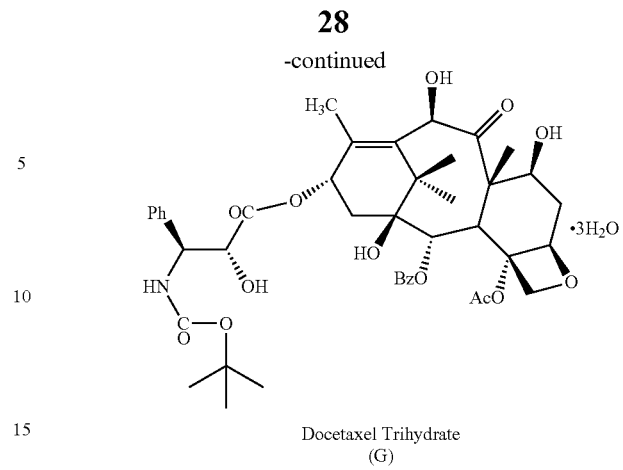

Docetaxel Trihydrate (G)

Charged 5.0 gm of docetaxel anhydrous and 16.5 ml of DMSO into a round bottom flask. Stirred the reaction mass to dissolve completely. Cool to 10-15° C. and start addition of 166 ml of water slowly for 1-2 hrs at 10-15° C. Maintain the temperature for 6 hrs. Filter the mass and suck dried. Then washed with water, air dried the material to get MC 5-7%.

We claim:

1. A process of preparation of docetaxel trihydrate (I)—

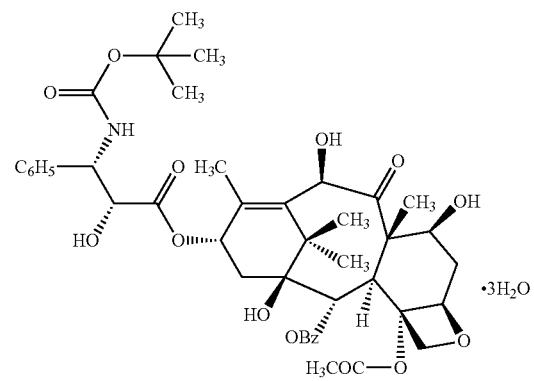

comprising the steps of—
  a. selectively chloroacylating 7 and 10 hydroxy functions of 10-Deacetyl baccatin III (or 10 DAB III) in halohydrocarbon solvent and pyridine to get (A);

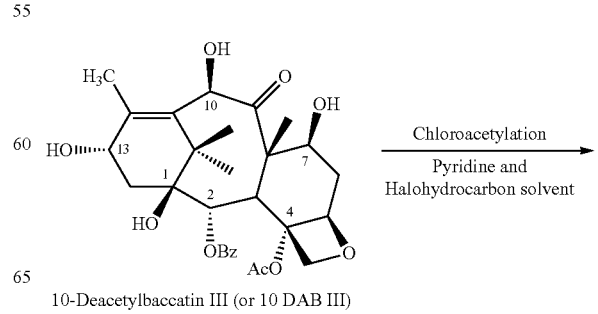

10-Deacetylbaccatin III (or 10 DAB III)

Chloroacetylation
Pyridine and Halohydrocarbon solvent →

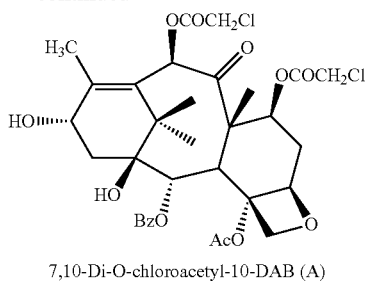

7,10-Di-O-chloroacetyl-10-DAB (A)

b. condensing (A) with benzyl protected side chain (B) in presence of a condensing agent and a moderator in an organic hydrocarbon solvent;

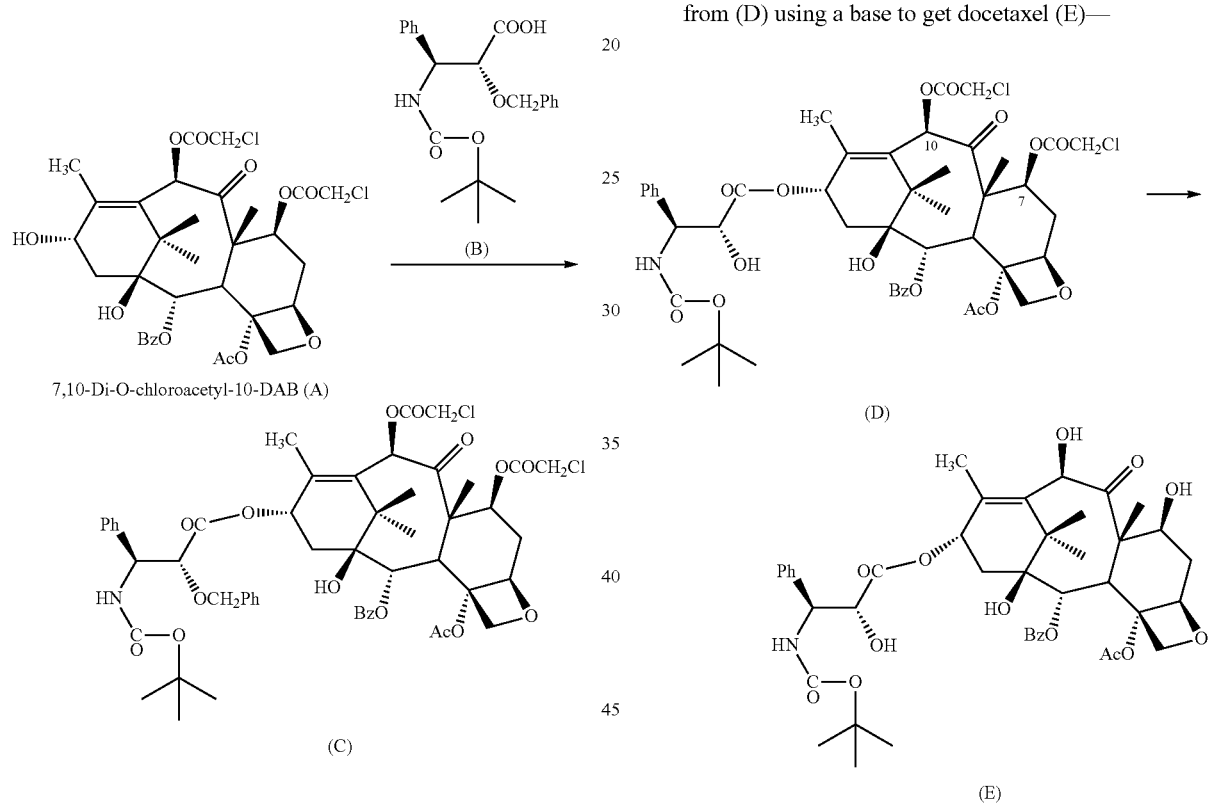

c. selective debenzylation of side chain using a reducing agent in an organic solvent to get (D);

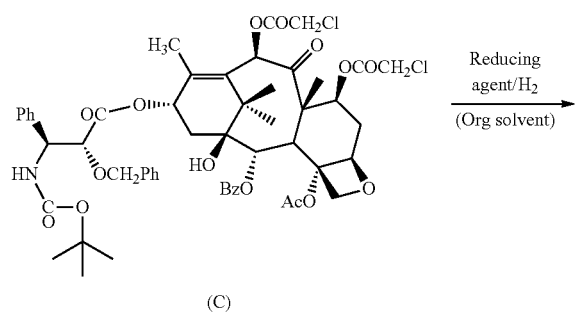

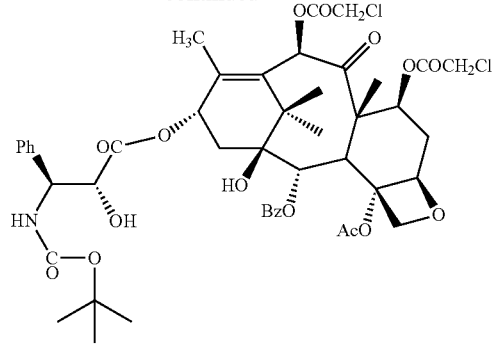

(D)

d. selectively deprotecting 7,10-di-O-chloroacyl group from (D) using a base to get docetaxel (E)— e. treating docetaxel (E) or purified docetaxel (F) in the presence of organic solvents selective from—2-alkoxy ethanol or dimethylsulphoxide and with water.

2. A process for preparing docetaxel trihydrate according to claim 1, wherein halohydrocarbon solvent of step a. is selected from dichloromethane, dichloroethane or the like.

3. A process for preparing docetaxel trihydrate according to claim 1, wherein condensing agent used in the step b. is selected from 4-Dimethylaminopyridine (DMAP) or HOBt (hydroxybenzotriazole).

4. A process for preparing docetaxel trihydrate according to claim 1, wherein moderator in the step b. is selected from N,N-Diisopropyl Carbodiimide (DIPC) or Dicyclohexyl Carbodiimide (DCCI).

5. A process for preparing docetaxel trihydrate according to claim 1, wherein an organic hydrocarbon solvent in the step b. is selected from toluene or xylene or benzene.

6. A process for preparing docetaxel trihydrate according to claim 1, wherein the benzyl protected side chain (B) in the step b. is added below the temperature of about 10° C.

7. A process for preparing docetaxel trihydrate according to claim 1, wherein the reaction temperature in the step b. ranges up to about 0° C. to about 20° C.

8. A process for preparing docetaxel trihydrate according to claim 1, wherein the selective deprotection of side chain using a reducing agent in the step c. comprise reducing agents selected from Pd on Charcoal, Rh or Ni.

9. A process for preparing docetaxel trihydrate according to claim 1, wherein the selective deprotection of side chain using a reducing agent in the step c. comprise hydrogen gas pressure ranging between 45 PSI to about 90 PSI.

10. A process for preparing docetaxel trihydrate according to claim 1, wherein the selective debenzoylation of side chain using a reducing agent in the step c. comprise an organic solvent selected from THF or THF ethanol mixture or THF, Ethanol and water mixture or DMF or Ethyl acetate.

11. A process for preparing docetaxel according to claim 1 wherein selectively deprotecting 7,10-di-O chloroacyl groups from Intermediate-Compound D, comprising use of base selected from ammonia or pyridine or mixture thereof.

12. A process for preparing docetaxel trihydrate according to claim 1, wherein selective deprotection of 7,10-di-O chloroacyl group from (D) in the step d. comprise a further purification of Compound E comprising the steps of—
1. Column purification using hydrocarbon solvent and ester solvent in combination as eluents
2. collecting and pooling the appropriate fractions
3. removing the solvents
4. add hydrocarbon or nitrile solvent to the residue
5. isolate the Compound E
6. optionally recrystallize with ketone and hydrocarbon solvent
7. adding isolated compound E in organic solvents selective from—2-alkoxy ethanol or dimethylsulphoxide
8. mix the reaction mass by stirring followed by cooling to 10-15° C.
9. start adding water maintaining the temperature 10-15° C.
10. after complete addition, maintain for at least 4-8 hours at temperature 10-15° C.
11. filter and isolate the docetaxel trihydrate.

* * * * *